United States Patent [19]
Uzgiris et al.

[11] Patent Number: 5,490,840
[45] Date of Patent: Feb. 13, 1996

[54] TARGETED THERMAL RELEASE OF DRUG-POLYMER CONJUGATES

[75] Inventors: Egidijus E. Uzgiris, Niskayuna; Lorinda R. Opsahl, Clifton Park; Kirby G. Vosburgh, Niskayuna; Thomas R. Anthony, Niskayuna; Harvey E. Cline, Niskayuna, all of N.Y.

[73] Assignee: General Electric Company, Schenectady, N.Y.

[21] Appl. No.: 312,362

[22] Filed: Sep. 26, 1994

[51] Int. Cl.⁶ .................................................. A61B 17/20
[52] U.S. Cl. .................. 604/22; 128/598; 128/660.03; 601/3; 607/97; 424/9.34
[58] Field of Search ............... 128/653.2, 653.4, 128/662.02, 660.03; 604/20, 22; 424/9; 601/2, 15, 3; 607/97, 901

[56] References Cited

U.S. PATENT DOCUMENTS

| | | | |
|---|---|---|---|
| Re. 33,590 | 5/1991 | Dom | 128/660.03 |
| 4,771,130 | 9/1988 | Cohen | 604/20 |
| 4,822,335 | 4/1989 | Kawaii | 604/20 |
| 4,925,922 | 5/1990 | Byers | 530/391 |
| 4,960,408 | 10/1990 | Klainer | 604/20 |
| 5,016,615 | 5/1991 | Driller | 604/20 |
| 5,145,863 | 9/1992 | Dougherty | 607/901 |
| 5,163,898 | 11/1992 | Marcos | 604/20 |
| 5,216,126 | 6/1993 | Cox et al. | 514/8 |
| 5,230,883 | 7/1993 | Kornguth | 128/653.4 |
| 5,247,935 | 9/1993 | Cline et al. | 128/653.2 |
| 5,275,165 | 1/1994 | Ettinger et al. | 128/653.2 |
| 5,307,812 | 5/1994 | Hardy et al. | 128/653.2 |
| 5,370,120 | 12/1994 | Oppelt | 128/660.03 |

OTHER PUBLICATIONS

Pimm, Malcolm. "Critical Reviews in Therapeutic Drug Carrier Systems", vol. 5, issue 3 (1988).
Lele, P. P., "Hyperthermiaby Utrasound", M.I.T.
"The Demonstration of Human Tumors on Nude Mice Using Gadolinium–Labelled Monoclonal Antibodies for Magnetic Resonance Imaging by S.Gohr–Rosenthal, H. Schmitt–Willich, W. Ebert & J. Conrad, Investigative Radiolog", vol. 28, No. 9, 789–795.

*Primary Examiner*—C. Fred Rosenbaum
*Assistant Examiner*—Chalin Smith
*Attorney, Agent, or Firm*—Lawrence P. Zale; Marvin Snyder

[57] ABSTRACT

Thermal drug treatment of tumor tissue is obtained by attaching a thermally active drug to carrier molecules which have an affinity to tumor tissue. Localized heating is performed on the tumor tissue, thereby activating the drug in the tumor tissue. The end result may be concentrated delivery of a drug to a chosen tissue, or, in the case where the drug creates a toxin when heated, selective tissue destruction of a selected locations heated. The localized heat may be applied by focused ultrasound heating.

5 Claims, 5 Drawing Sheets

TARGETED THERMAL RELEASE OF DRUG-POLYMER CONJUGATES

CROSS REFERENCES TO RELATED APPLICATIONS

This application is related to co-pending U.S. patent applications "Method Of Enhanced Drug Delivery To Tumor Tissue With High Charge Macromolecules" by Uzgiris Ser. No. 08/312,367, filed Sep. 26, 1994; and "Image Guided Thermal Release Of Drugs From Targeted Liposomal Drug Carriers" by Opsahl, Uzgiris Ser. No. 08/312,369, filed Sep. 26, 1994; and "Method Of Maximizing Tumor Contrast With High Charge Macromolecules" by Uzgiris Ser. No. 08/312,361, filed Sep. 26, 1994; "Method Of Maximizing Tumor Contrast With Contrast Agents Of High Molecular Weight" by Uzgiris, Opsahl Ser. No. 08/312,368 filed Sep. 26, 1994 all assigned to the present assignee and hereby incorporated by reference.

BACKGROUND OF THE INVENTION

1. Field of the Invention

The present invention relates to medical treatment of tumor tissue, and more specifically, deals with optimizing tissue destruction with focused ultrasound heating.

2. Description of Related Art

Devices have been developed which focus ultrasonic sound waves at a focal point deep within a subject. At the focal point, energy is dissipated and local heating results. Of the tissue is allowed to come to a sufficiently high temperature for a sufficiently long period of time, the tissue will be denatured and be re-absorbed by the body. In this manner, tumors can be killed as without the necessity of an operation.

In some cases, it may not be possible to locally heat a tumor to a high enough temperature without causing serious damage to the patient. For example, a tumor tangled around the brain stem may not be treatable by this method because of the danger of thermal damage to the brain stem.

Another method of destroying tumor tissue is through chemotherapy. In conventional chemotherapy, a patient is injected with a poisonous compound that concentrates in the faster growing tissue of a tumor. The dose of the poisonous compound is adjusted such that the concentration in the normal tissue does not reach toxic levels while the concentration in the tumor is high enough to destroy it.

One alterative to simple chemotherapy is photodynamic therapy where the body is injected with a photosensitive compound that tends to concentrate in the tumor. The primary photosensitive compound itself is harmless. However, when the compound is exposed to light, it breaks down into successor compounds at least one of which is toxic to the tissue. By concentrating light on the tumor, the compound break down and toxicity are limited to the tumor. One problem with this approach is that the patient is largely opaque and any light that is transmitted by the body is highly scattered and diffuse. Consequently, it is difficult to expose tumors in many parts of the body to light.

In many medical procedures, it is important to accumulate a certain chemical entity to a desired tissue type. In chemotherapy, it is important to deliver drugs to a cancerous tumor tissue. Traditional anti-tumor therapies, including chemotherapy and radiation treatments, rely upon a differential response between normal tissue and cancerous cells. However, there remains unavoidable toxicity towards normal tissue which causes substantial side effects and limit practical drug dosages.

Much work has been done in the area of developing specific chemical entities attached to antibodies, that are specific to tumor antigens. Delivery of chemical entities by this method is a difficult task since it requires finding antibodies which are specific to tumor antigens, and do not bind to other tissue. For most human tumors, the associated antibodies are not specific only to this type of tissue.

A further problem is that once antibody has been found that binds to the type of tumor intended to be destroyed, the delivery of the chemical entity may not be very large since the density of the antibodies on the surface of the cells of tumor tissue is generally not high.

Currently there is a need for a method of treatment of tumor tissue of a subject with limited collateral damage to adjacent tissues of the subject.

SUMMARY OF THE INVENTION

Drug molecules are accumulated in tumor tissue of a subject, then heated by localized focused ultrasound heating to cause the drug to be activated, or released from, a carrier causing an increased concentration of the drug in the heated region, as opposed to other regions of the subject. Carrier molecules may be used to facilitate the accumulation of the drug in the tumor tissue. The carriers are chosen to preferentially accumulate in tumors through enlarged pores in the blood vessels of the tumor tissue, but remain in the vessels in normal tissue. Drug molecules are conjugated to carrier molecules through a labile bond that can be readily broken at mildly elevated temperatures above the subject's body temperature. Thus drug release, or toxin creation, could be adjusted depending upon the temperature of the location being heated.

OBJECT OF THE INVENTION

It is an object of the present invention to provide a method of selectively destroying tissue within a living subject using focused ultrasonic heating of chemical compounds injected into the subject at lower temperatures than are possible with focused ultrasound heating alone.

It is another object of the present invention to provide method of selectively destroying tissue within a living subject that reduces collateral damage in surrounding tissue.

It is another object of the present invention to provide an increased concentration of a drug within tumor tissue as compared with other tissue of the patient.

It is another object of the present invention to provide a method for selectively destroying cancerous tissue within a subject.

It is another object of the present invention to selectively deliver large concentrations of therapeutic drugs to tumor tissue, with limited side affects on adjacent tissue.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawing, in which:

DETAILED DESCRIPTION OF THE INVENTION

Figure 1:
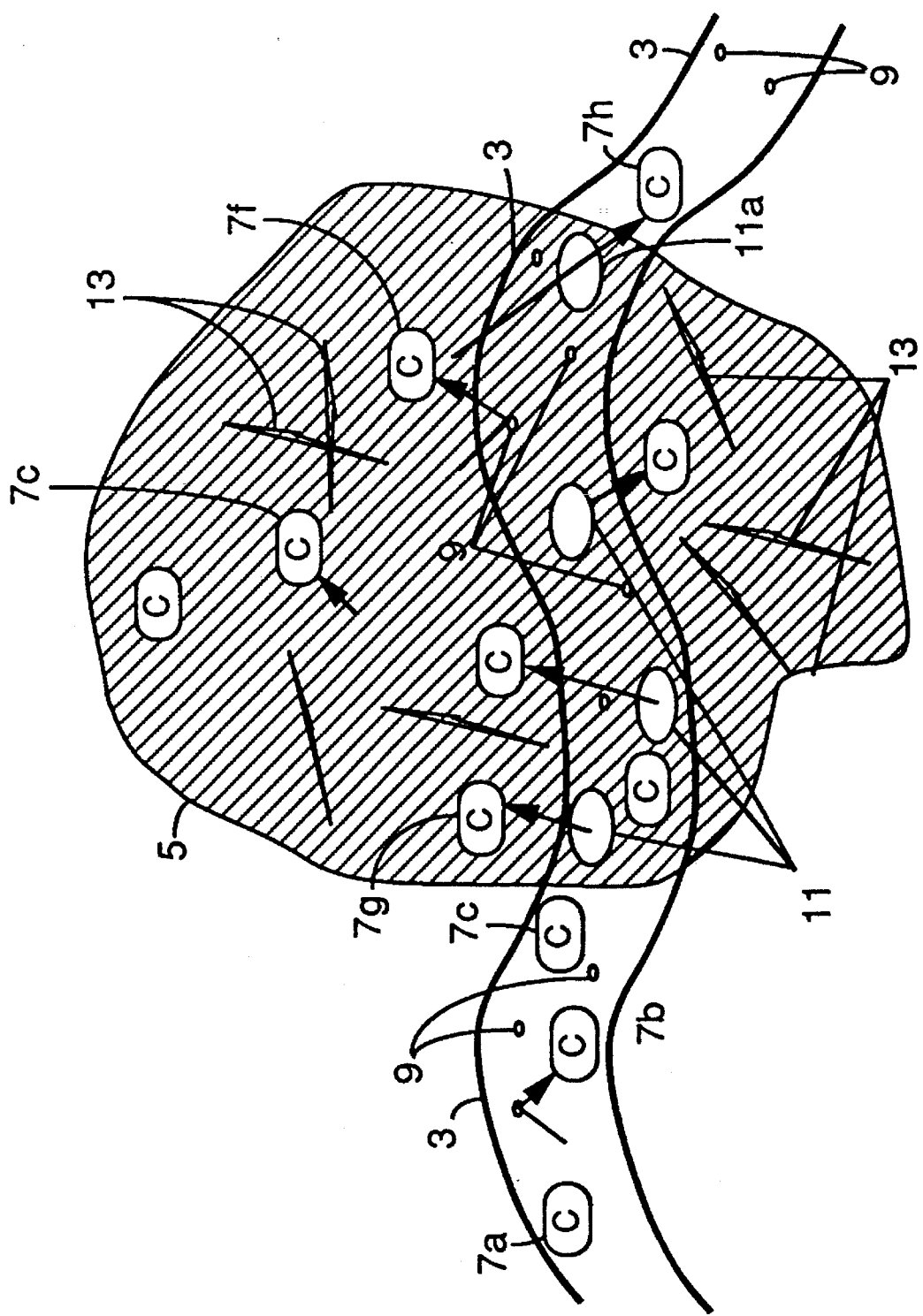
FIG. 1 is an illustration of drug/carrier molecule complexes delivery to tumor tissue.

Although the body is opaque to light, it is often transparent to ultrasonic waves. If ultrasound waves are emitted from a focused ultrasound transducer or a phased array, they can be concentrated at any location in the body and cause local heating there. If the body is injected with a thermally metastable compound that tends to naturally concentrate in the faster growing tissue of the tumor while these ultrasonic waves are concentrated on a tumor, the compound will break down and only produce toxic reaction products in the tumor tissue. If $C_T$ is the ratio of the concentration of the metastable compound in the tumor as compared to normal tissue and $C_R$ is the ratio of the decomposition rate at temperature T in the tumor versus the normal body temperature $T_0$, then the concentration ratio R of toxic reaction products in the tumor relative to normal tissues is given by:

$$R = C_T C_R \qquad (1)$$

R must be greater than 1 for the method to function. $C_R$ can be less than 1, but preferably as high as possible. $C_R$ can vary from 0.1–1000. Preferably $C_R$ and $C_T$ will be chosen such that R is very high. The decomposition rate ratio is given by:

$$C_R = EXP[\Delta G/R(T-T_0)/(T\, T_0)] \qquad (2)$$

where $\Delta G$ is the free energy of the chemical reaction.

The combination of equations (1) and (2) yield the ratio R of the toxic compound in the tumor to the other tissues in the body.

$$R = EXP[\Delta G/R(T-T_0)/(T\, T_0)]C_R \qquad (3)$$

As an example, consider a chemical reaction with a free energy change of $\Delta G=25$ kcal/mole. If the temperature in the tumor is raised by 10 degrees Centigrade by the ultrasonic heating over the normal tissue temperature of 36 Centigrade, the enhancement of toxic reaction products in the tumor is a factor of 3.55X. If $\Delta G=15$ kcal/mole, the enhancement is 2.14X. This enhancement could be used either to raise the toxicity level in the tumor or to lower the toxicity level in the healthy tissue. Compounds would be synthesized that had free energy of reactions that are low enough to be thermally decomposed but large enough to significantly increase the toxicity level in the tumor. Suitable free energies of reaction would be from 5 to 50 Kcal/mole.

The present invention enhances drug delivery to tumor tissue and consequently, tissue destruction, by causing an elevated concentration of the drug in the tumor tissue. This may be done by injecting a metastable compound and then perform localized heating which induces breakdown of a metastable compound into a toxin only where heated.

The present invention takes advantage of the differences in tumor tissue from normal tissue to cause additional accumulation of the drug in the tumor tissue. Tumors tend to have vasculature which has much larger pores and tend to be 'leaky'. The use of a small molecule, for chemotherapy treatment causes it to pass out into the tumor interstitial spaces and readily migrates its way back into the vasculature and is removed from the region. The drug is attached to a carrier molecule, with a labile bond. The carrier molecules have an affinity to tumor tissue. In the aforementioned U.S. patent applications, "Method Of Maximizing Tumor Contrast With Contrast Agents Of High Molecular Weight" by Uzgiris, Opsahl Ser. No. 08/312,368; and "Image Guided Thermal Release Of Drugs From Targeted Liposomal Drug Carriers" by Opsahl, Uzgiris Ser. No. 08/312,369; the importance of molecular size of the carrier and molecules, in causing them to accumulate in tumor tissue through the enlarged pores of tumor vasculature, and thereby become 'trapped' within the tumor tissue interstitium is described. Also, in the aforementioned U.S. patent applications "Method Of Enhanced Drug Delivery To Tumor Tissue With High Charge Macromolecules" by Uzgiris Ser. No. 08/312,367; and "Method Of Maximizing Tumor Contrast With High Charge Macromolecules" by Uzgiris Ser. No. 08/312,361 it was shown that chemical entities (a drug and a contrast agent, respectively) may be 'piggybacked' on a sufficiently charged carrier molecule to result in a carrier/chemical entity complex having a net negative charge to further increase accumulation of the carrier/chemical entity in the tumor tissue, along with cause increased retention in the tumor tissue.

The carrier molecules are chosen to have a size such that they would not leak from the blood vasculature through pores in normal tissue but would do so through the larger pores of tumor vasculature and would accumulate over a period of time in the tumor interstitium. The carrier molecules are also of such a size that they do not readily re-enter the post capillary circulation as do small molecules. A size of approximately 100 nm diameter was chosen which distribute preferentially into cancer tissue due to the leaky nature of tumor vasculature. This, together with an ineffective lymphatic drainage system in tumor tissue, results in the retention of carrier molecules for an extended period of time as compared with small molecules.

In FIG. 1, a plurality of complexes of carrier molecules attached to drug molecules encapsulating an amount of a drug, is shown as "C". A solution of complexes, $7a, 7b, 7c$ is introduced into a patient's blood vessel 3. These complexes follow blood vessel 3 and are contained by blood vessel 3 since pores 9 in normal tissue are a size small enough to contain complexes $7a, 7b, 7c$. Once the complexes enter tumor tissue 5, pore size becomes enlarged shown as pores 11. Complexes $7d$ and $7g$ pass through pores 11 and into interstitial space of tumor 5. Complex $7e$ is shown working its way through the interstitial space of tumor 5. Stroma 13 typically develops in tumor 5 thereby further entangling and holding complexes within the interstitial spaces. The clearance of small molecules from the tumor interstitium is rather rapid. Complexes according to the present invention are able to leak into the tumor interstitium, but their clearance from the tumor is retarded due to their size. Complexes do not readily exit the tumor interstitium by the route of post capillary drainage, which is the dominant route of clearance of small molecules from the interstitial space of tumor tissue. Eventually, the complexes may be cleared through the residual lymphatic drainage that may be present in the tumor tissue. If the complex are chosen to be very large, however, they may never fit through the pores of the vasculature and would be excluded from the interstitial space of tumor 5.

Conventional Magnetic Resonance (MR) Imaging provides a radiologist with internal views of a patient's anatomy. MR imaging provides excellent contrast between different tissues and is useful in planning surgical procedures. A tumor in a patient is much more visible in an MR image than as seen in actual surgery because the tumor and normal tissue often look similar in surgery. The tumor can also be obscured by blood during surgery.

A view of the heated region may also be provided with the use of MR temperature sensitive pulse sequences. MR imaging temperature-sensitive pulse sequences are described in U.S. Pat. No. 5,307,812 May 3, 1994 "Heat Surgery System Monitored by Real-Time Magnetic Resonance Profiling" by C. Hardy, H. Cline which describes capturing temperature mapped images of a subject.

In U.S. Pat. No. 5,247,935 Sep. 28, 1993 "Magnetic Resonance Guided Focused Ultrasound Surgery" by H. Cline, R. Ettinger, K. Rohling, R. Watkins; and U.S. Pat. No. 5,275,165 Jan. 4, 1994 "Magnetic Resonance Guided Ultrasound Therapy System With Inclined Track to Move Transducers in a Small Vertical Space" by R. Ettinger et al., assigned to the present assignee and hereby incorporated by reference, an ultrasound transducer is positioned within an MR Imaging magnet with the use of hydraulics so as to focus ultrasound heat to a specific location selected by the operator. Since an MR imaging system is employed, internal structures may be imaged. Also, since temperature-sensitive MR pulse sequences may be used, a heated region may also be imaged and registered with a conventional MR image providing feedback of the location being heated.

Figure 2:
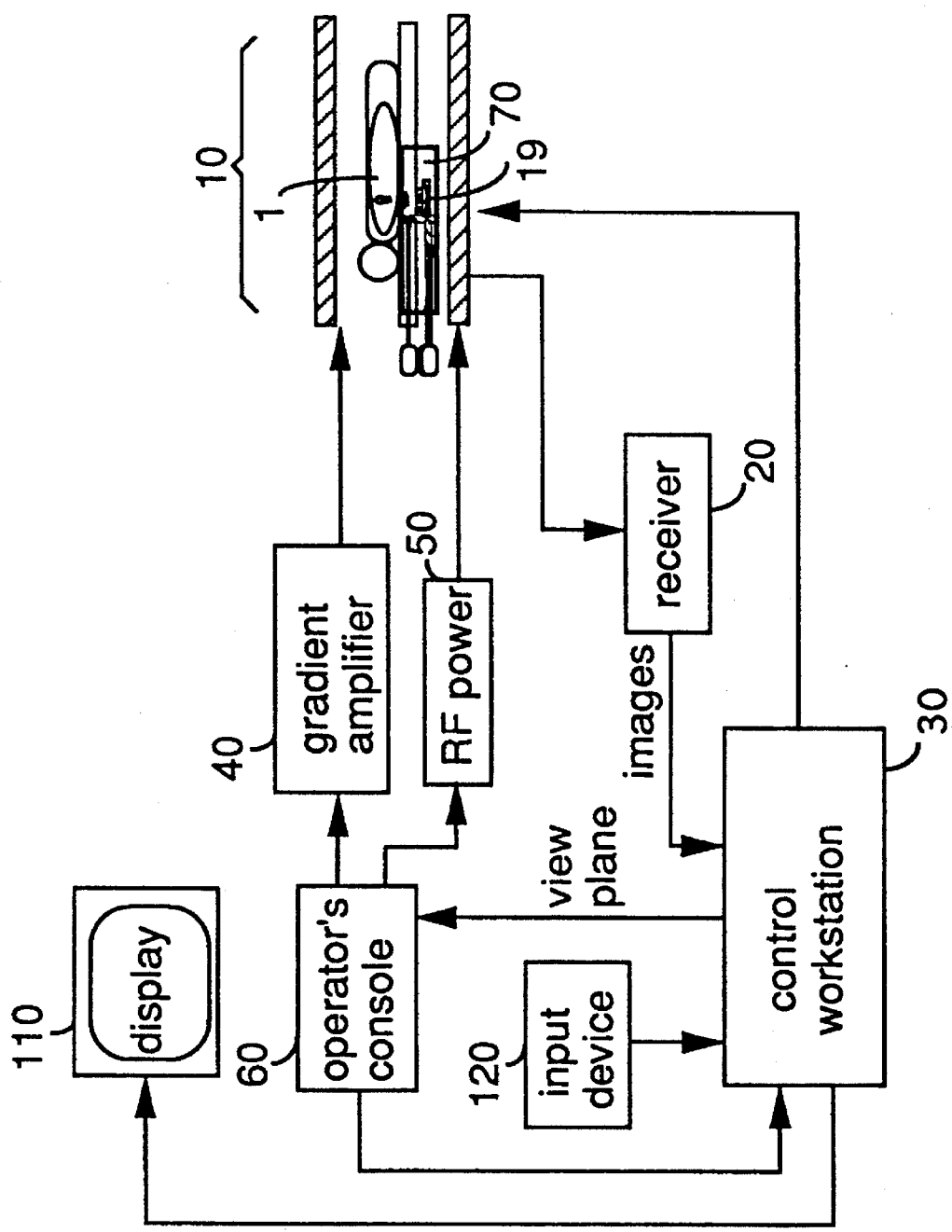
FIG. 2 is a schematic block diagram of an MR Therapy system compatible with use of the present invention.

A schematic block diagram of an MR therapy system is shown in FIG. 2. An MR imaging system 10 employs pulse sequences in the well known manner to rapidly acquire images of a patient 15. A gradient amplifier 40 and a radiofrequency (RF) power source 50 supply the power for the sequences. An operator console 60 is used to control the imaging system. Raw data is sent from receiver 20 to a control workstation 30 that displays images on a display means 110 to a surgeon. Control workstation 30 may compute a path from transducer 19 to a desired location within patient 15 which avoids bone and air spaces. The surgeon indicates the desired location of the focal point of ultrasound transducer 19 by means of an input device 120 which can be a three-dimensional pointing device such as a track ball or a mouse.

Control workstation 30 actuates a positioning means 70 to position ultrasound transducer 19. MR imaging system 10 then employs pulse sequences to rapidly acquire temperature sensitive images of patient 15. Since both the internal structures and heated regions are imaged, the surgeon can accurately position the heated region to correspond to a desired internal structure through input device 120.

Figure 3:
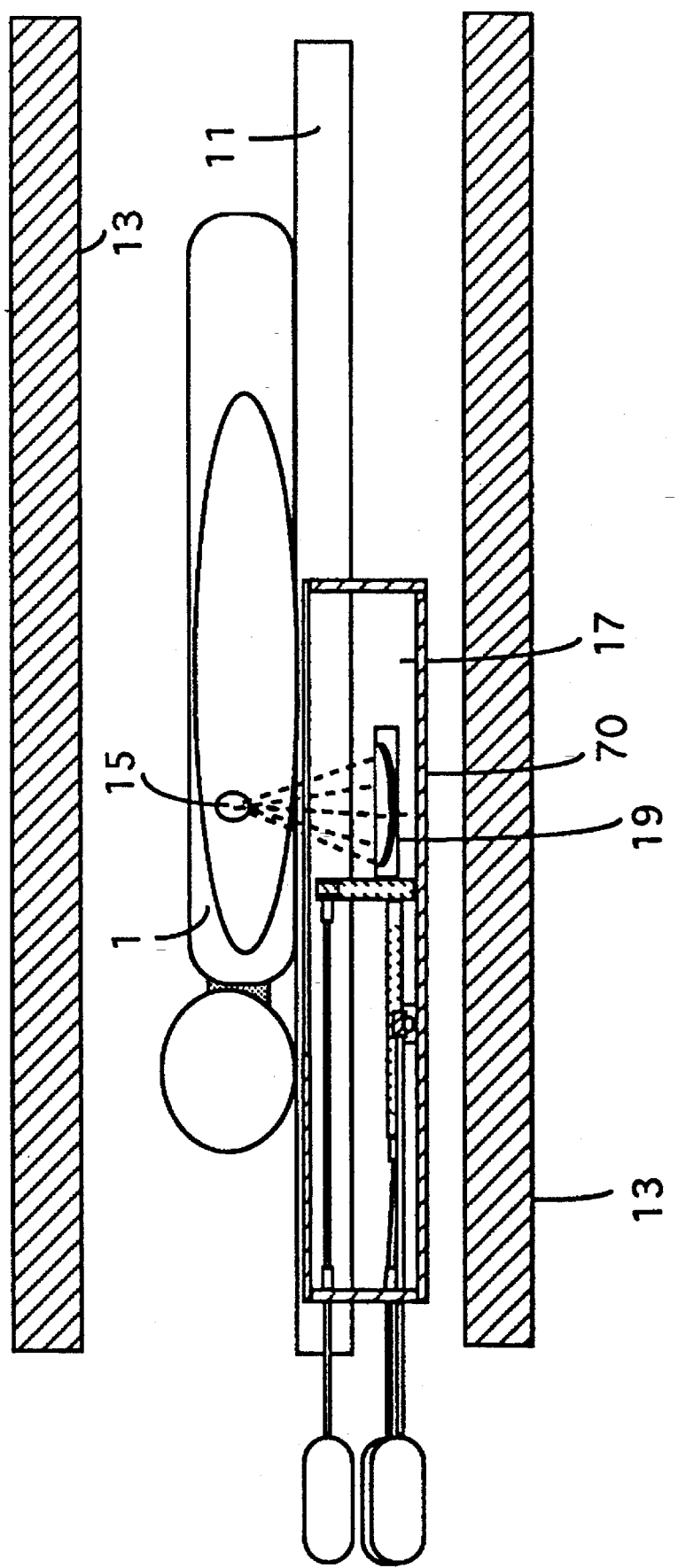
FIG. 3 is an illustration of a patient positioned within the bore of the magnets of the MR Therapy system of FIG. 2 as the patient would appear during localized heating of a desired location of the patient.

As shown in FIG. 3, patient 15 is placed on a table 11 designed to accommodate focused ultrasound transducer 19 in an ultrasound conducting liquid bath 17. Ultrasound conducting liquid 17 is chosen to be one that will conduct ultrasonic energy with little attenuation. Ultrasound transducer 19 can be moved inside the bore of an MR imaging magnet 13 by positioning means 70 to focus on different locations within patient 15. The focal point of ultrasound transducer 19 is positioned along the computed path by positioning means 70 onto a tumor 15. The ultrasound transducer is moved while the surgeon views temperature sensitive images.

It is now possible to accurately view tumor tissue with MR imaging, heat deep lying tumor tissue with focussed ultrasound, and adjust the location of heat application by viewing temperature sensitive MR images superimposed upon conventional MR images. This would allow the operator to adjust the location of the ultrasound focus to correspond to the tumor tissue.

By selectively heating the tumor tissue, the labile bond is broken and the drug is released. Release is effectuated in locations having a high temperature, and very little where there is normal body temperature. By specifically localizing the heat, it is possible to achieve a much larger concentration of the drug in the tumor tissue as compared with other tissues which are not heated.

Figure 4:
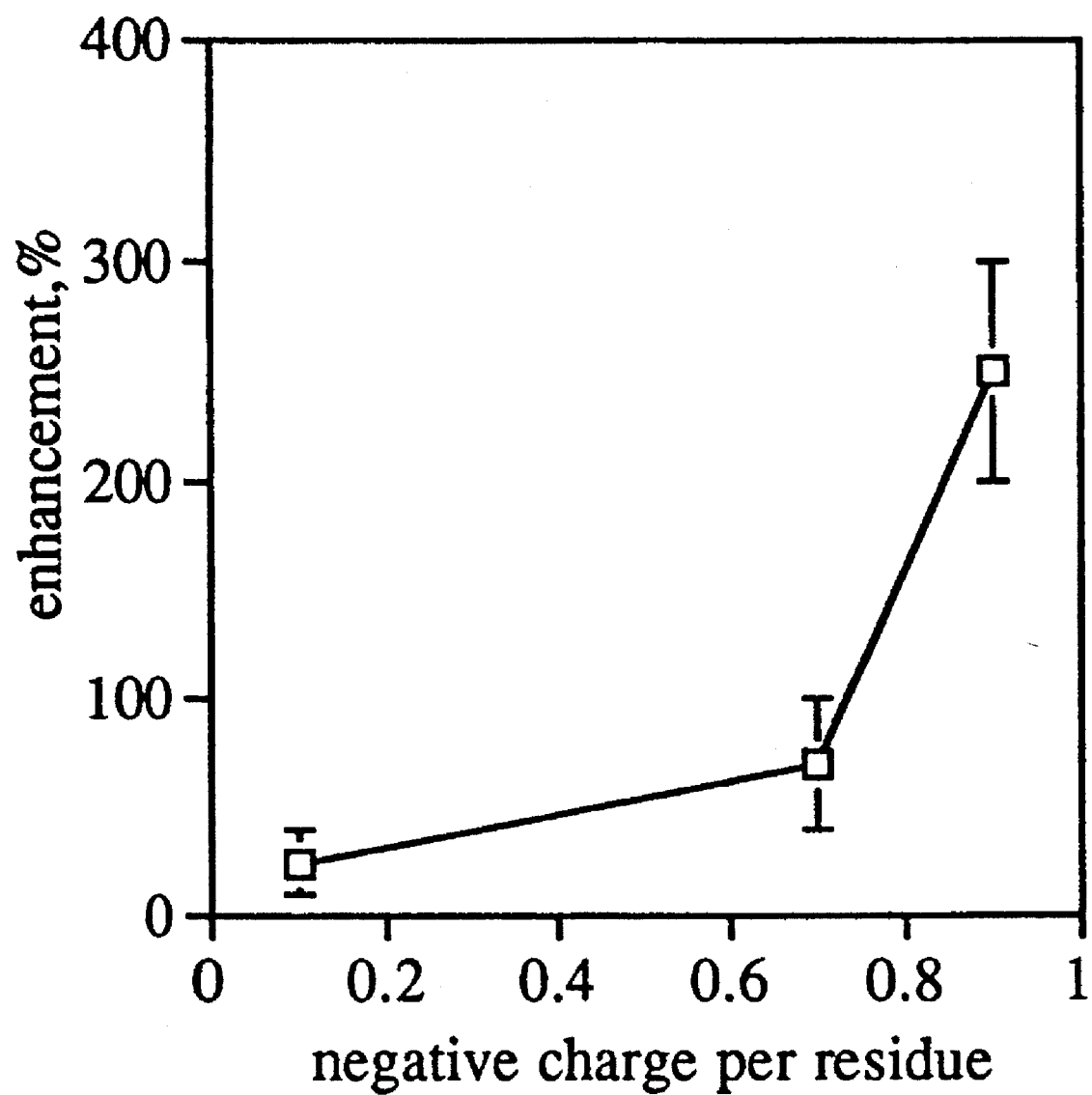
FIG. 4 is a graph of percentage of a drug released over time at different applied temperatures.
Figure 5:
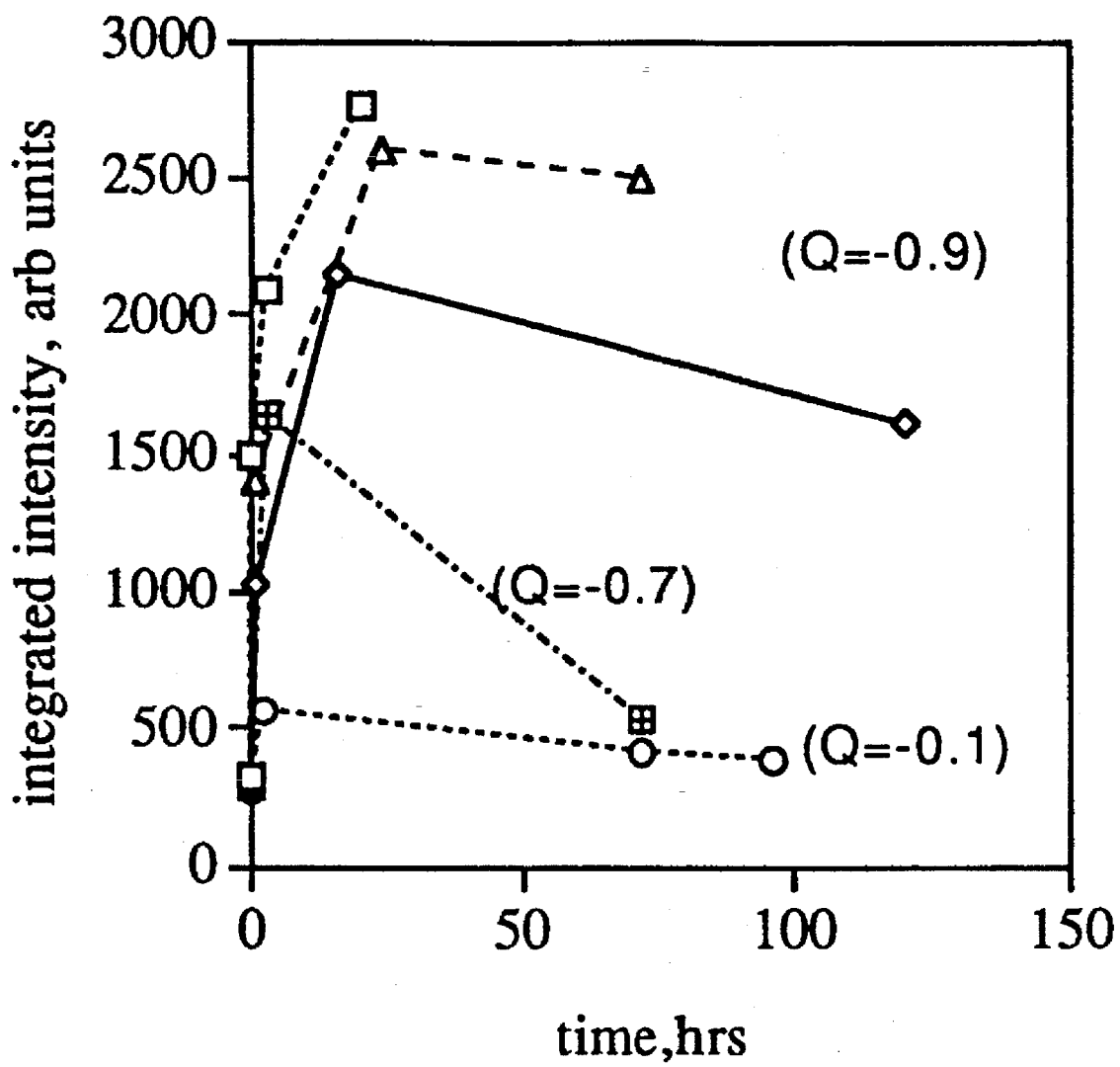
FIG. 5 is a graph of the accumulated amount of a drug released after one hour as a function of temperature.

Carrier molecules may be polylysine, human serum albumin (HSA), dextran, or other similar sized polypeptides. Experiments were performed using fluorescein isothiocyanate (FITC) conjugated rabbit imunoglobin G (IgG) molecule. The conjugation is through a thio-urea bond, that is the isothiocyanate moiety links to an amine group of the protein such that the bond is: {fluorescein}-N-CS-N-{protein}. At 4° C. the bond is stable, but at elevated temperatures the FITC is released from the protein as shown in an assay performed by filtering the test solution through an Amicon 30,000 kDa cutoff membrane filter. The release rate at different temperatures is shown in FIG. 4. The cumulative release after one hour exposure to different temperatures is shown in FIG. 5. At approximately 55° C. there is an efficient release of the FITC from the macromolecule.

The present invention may function in two different modes. It may act primarily as a drug delivery system in which elevated dosages of a toxic chemical are delivered to tumor tissue. It may also act primarily as a thermal tissue destruction system which destroys tissue at its focal point aided by the drug delivered to the tumor tissue. Both modes minimize side effects due to drug interaction with normal tissue. Beneficial synergistic effects are anticipated through the simultaneous use of minimally-invasive thermal therapies and drug release.

While specific embodiments of the invention have been illustrated and described herein, it is realized that modifications and changes will occur to those skilled in the art. It is therefore to be understood that the appended claims are intended to cover all such modifications and changes as fall within the true spirit and scope of the invention.

What we claim is:

1. A method of thermal drug treatment of tumor tissue of a subject comprising the steps of:

a) selecting drug molecules used in tumor tissue treatment of living subjects;

b) selecting a polypeptide carrier molecule of a size such that it will pass freely into tumor tissue but substantially none will pass into normal tissue;

c) binding drug molecules to carrier molecules to result in combined carrier/drug molecules;

d) introducing the carrier/drug molecules into a blood vessel of said subject having said tumor tissue desired to be destroyed causing the carrier/drug molecules to infuse into the tumor tissue; and e) heating the tumor tissue employing focused ultrasound and the carrier/drug molecules within the tumor tissue to cause the carrier/drug molecules to produce a toxin having a relatively increased concentration in the tumor tissue as compared with the concentration in other tissues of said subject.

2. The method of thermal drug treatment of claim 1 wherein the polypeptide carrier molecules are chosen to have a plurality of residues such that the combined charge of molecules of the selected polypeptide and selected drug is a net negative charge.

3. The method of thermal drug treatment of claim 1 wherein the polypeptide carrier molecules and drug molecules have a combined molecular size chosen to selectively accumulate in the tumor tissue.

4. The method of thermal drug treatment of claim 1 wherein the polypeptide carrier molecules are selected to be polylysine molecules having a plurality of attached residues.

5. The method of thermal drug treatment of claim 1 wherein the drugs are chosen to be chemotherapy drugs.

* * * * *